(12) United States Patent
Hanneman et al.

(10) Patent No.: US 7,093,598 B1
(45) Date of Patent: Aug. 22, 2006

(54) APPLICATOR FOR TRACH DRAIN SPONGE

(76) Inventors: Jeanne Hanneman, 11828 Presley Cir., Plainfield, IL (US) 60544; Marie Conn, 1054 Sycamore St., P.O. Box 82, Beecher, IL (US) 60401

( * ) Notice: Subject to any disclaimer, the term of this patent is extended or adjusted under 35 U.S.C. 154(b) by 0 days.

(21) Appl. No.: 11/077,816

(22) Filed: Mar. 11, 2005

(51) Int. Cl.
*A61M 16/00* (2006.01)

(52) U.S. Cl. ............................. 128/207.29; 128/207.14

(58) Field of Classification Search .......... 128/200.26, 128/202.27, 202.28, 207.14, 207.15, 207.16, 128/207.29, DIG. 6, 912, DIG. 26, 207.17; 600/201; 604/77, 79, 174, 177, 179; 30/129, 30/137, 147, 148, 150, 322
See application file for complete search history.

(56) References Cited

U.S. PATENT DOCUMENTS

| | | | |
|---|---|---|---|
| 2,248,685 A * | 7/1941 | Lunz ............................ | 30/129 |
| 3,422,817 A * | 1/1969 | Mishkin et al. ............. | 128/846 |
| 3,890,960 A * | 6/1975 | Wunsch et al. ............. | 600/191 |
| 4,610,252 A * | 9/1986 | Catalano ..................... | 606/157 |
| 4,941,882 A * | 7/1990 | Ward et al. .................. | 604/180 |
| 5,058,579 A * | 10/1991 | Terry et al. ............. | 128/207.14 |
| 5,254,115 A * | 10/1993 | Bhatta et al. ................. | 606/16 |
| 5,918,599 A * | 7/1999 | Shesol .................... | 128/207.17 |
| 6,725,862 B1 | 4/2004 | Klinberg et al. | |

* cited by examiner

*Primary Examiner*—Henry Bennett
*Assistant Examiner*—Amadeus Lopez
(74) *Attorney, Agent, or Firm*—Patzik, Frank & Samotny Ltd.

(57) ABSTRACT

The invention relates to a device and a method of use that will allow a medical professional to change a patient's Tracheostomy dressing in an efficient manner that will cut down both the professional's and patient's discomfort. In the preferred embodiment of the invention, the device has a body that includes a handle, a shoulder and two prongs, however, the handle is optional. The entire lower surface of the body has a concave curve in one embodiment. The handle extends and ends at the shoulder. On the end of the shoulder, extending away from the shoulder, and curving in an upward direction relative to the shoulder, are the two prongs. The prongs are parallel to one another and form a "U"-shape, the distance of which is wider than the distance of the diameter of a trach tube. The prongs are designed to fit within the trach drainage sponge. This allows the user of the device to insert the sponge in a simple, smooth manner. After successfully inserting the sponge into position, the professional will remove the device, leaving behind the sponge.

24 Claims, 7 Drawing Sheets

APPLICATOR FOR TRACH DRAIN SPONGE

FIELD OF INVENTION

This invention relates to an apparatus and a method for the application of a trach drainage sponge to a patient. In particular, the invention relates to the application of the trach drainage sponge to the patient's neck between the trach apparatus and the neck.

BACKGROUND

A tracheostomy is an opening through the neck into the trachea. A physician may perform the operation as an emergency room procedure or as a scheduled operation. Specifically, a surgeon will make an incision into the trachea through the neck below the larynx. The physician makes the incision through the skin and, in particular, through the second, third or fourth tracheal ring. An actual small hole is made in the fibrous tissue of the trachea, and the opening is then dilated to allow the intake of air. The physician usually will then insert an indwelling tube into the opening to allow continuous increased air flow.

The trachea or "trach" apparatus (i.e., the tube) usually will be held in place by a restraint strap or band (usually made of fabric, but may be some other type of material) placed around the patient's neck. As can be plainly understood, the incision and the subsequent insertion of the trach apparatus will lead to a large amount of bleeding by the patient. To prevent infection, airway restriction and increase the patient's comfort, a medical professional will change the dressing around the wound on a fairly consistent basis. The dressing is positioned between the patient's neck and a plate on the trach apparatus. The restraint strap extends around the patient's neck, with the ends secured to opposite sides of the trach apparatus, typically at the plate. The dressing is positioned between the patient's neck and the trach plate and strap, under tension induced by the restraint strap.

In the prior art, the medical professional usually changed the dressing, which includes a trach drain sponge, at least three times per day. When changing the sponge, the medical professional follows a typical clean procedure. Under the clean procedure, the medical professional must ensure the use of clean, scrubbed hands and instruments. The procedure takes the medical professional approximately five to ten minutes to perform; however, in this prior art method, both the medical professional and the patient are subjected to a good deal of discomfort during the performance of the procedure.

During the performance of the prior art procedure, the medical professional is forced to lean over near the patient's neck. Obviously, the professional has to take great care in removing the trach drainage sponge and inserting a new one between the patient's neck and the trach apparatus. The professional has to make room under the band holding the tube in place and then carefully adjust the new sponge to make sure of a proper fit, all the while trying to avoid jarring the patient or the tube in the patient's neck. This procedure resulted in body aches and pain for the professional as well as an increased stress level. In addition, as hard as the professional might try, the professional often jarred the patient and/or the tube, causing the patient great discomfort.

SUMMARY OF THE INVENTION

The invention disclosed herein offers an alternative to the difficult, stressful and painstaking process of changing the trach apparatus dressing and, in particular, the trach drainage sponge. The invention relates to a device and a method of use that will allow the medical professional to change the patient's dressing in an efficient, fast, accurate manner that will cut down on the professional's and patient's discomfort, save time in changing the dressing and will do so in a very cost efficient manner.

In the preferred embodiment of the invention, the device has a body. The body has an upper surface, a lower surface, a first and second side, a proximal end and a distal end. The body generally includes a handle, a shoulder and two prongs, however, the handle is optional. The entire lower surface of the body has a concave curve in the preferred embodiment, but the curve can be limited to the shoulder, the prongs or can be eliminated altogether in other embodiments. The concave curve extends particularly from one side to the other side.

For ease of use, the handle may have a gripping mechanism, usually a thumb groove, to provide the medical professional or other user of the device a better grip, but, in other embodiments of the device without a handle, the shoulder also could include a thumb groove to provide better griping. The handle also has a proximal and a distal end, the proximal end being the same as the proximal end of the body. The distal end of the handle ends at the shoulder.

On the distal end of the shoulder, extending away or distally from that distal end of the shoulder, and curving in an upward direction relative to the shoulder, are two prongs. Each prong has an inner and an outer edge. The prongs are parallel to one another and generally form a "U"-shape. Most trach tubes have a certain diameter and, in the preferred embodiment, the prongs are separated by a distance wider than the distance of the diameter of the trach tube. In this manner the prongs easily fit around the trach tube. Furthermore, since the device is preferably made of plastic, it can be molded inexpensively and quickly to fit various size and shapes of trach tubes—i.e. a medical professional likely will require a smaller device for a child.

Moreover, the prongs fit within the typical trach drainage sponge. A typical trach drainage sponge has two sheaths, an upper sheath and a lower sheath. The prongs fit between the sheaths with the top sheath resting on the prongs. This allows the user of the device to insert the dressing and the sponge in a simple, smooth manner. Specifically, once the medical professional has removed the old dressing from around the trach apparatus, the professional will insert the prongs between the top sheath and lower sheath. The professional also may pinch the sponge against the body of the device. In this manner, the professional will have greater control over the sponge. If necessary, the professional may slightly raise the restraint mechanism from its normal position to make room for the insertion of the device and sponge combination.

The device/sponge combination may be inserted in an arcing motion between the trach plate and the patient's neck. After successfully inserting the sponge into position, the professional will remove the device, leaving behind the sponge. This process is one fluid motion and can be accomplished quickly and efficiently without the need to readjust or reposition the sponge, which could lead to the discomfort (for both the professional and patient) as described above.

DETAILED DESCRIPTION

Figure 1:
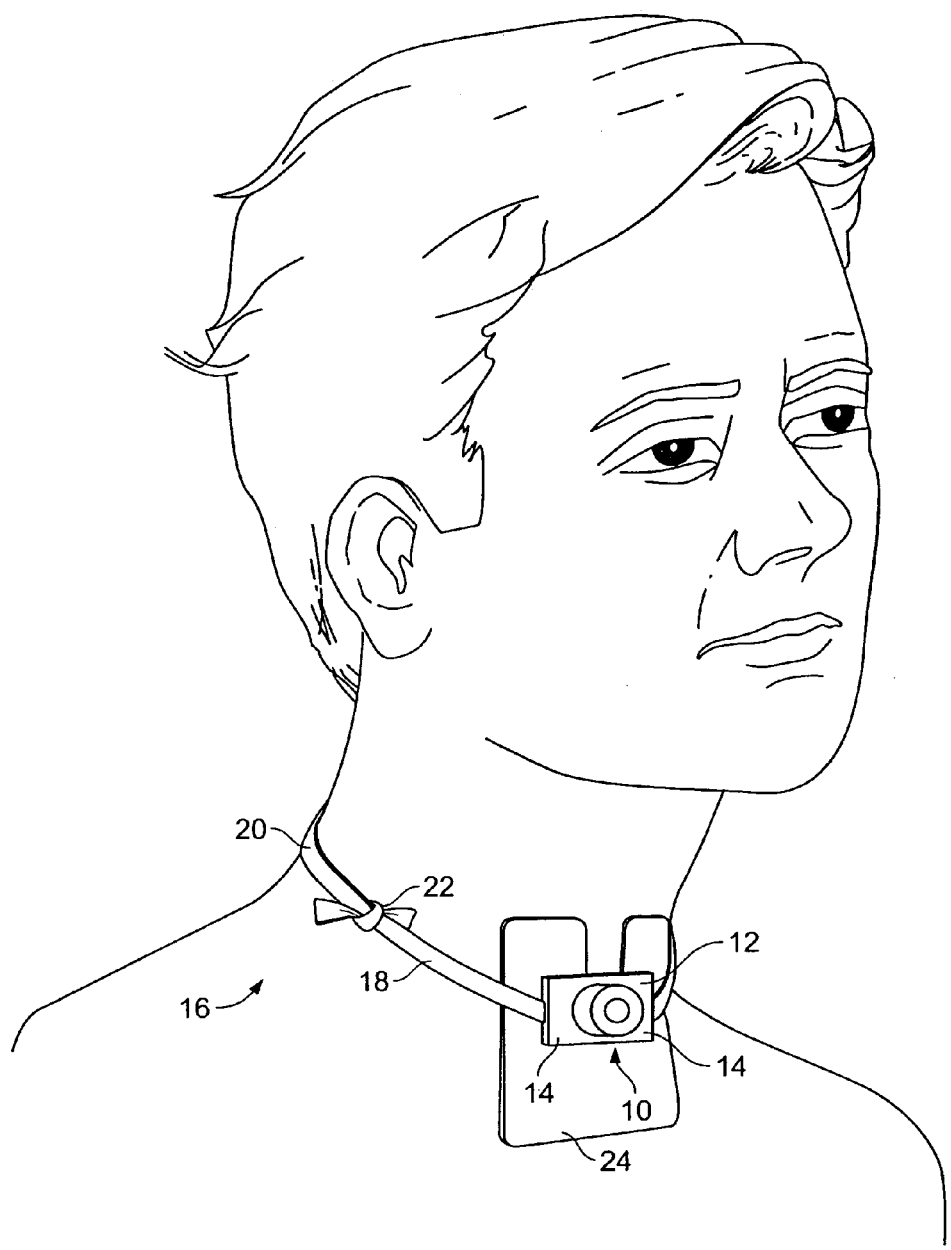
FIG. 1 is a view of a patient with a tracheostomy as is known in the art.

FIG. 1 is a perspective view of a patient with a tracheostomy tube 10 shown extending from the patient's neck. The tracheostomy tube includes a plate 12. The plate includes a first side and second side 14. A restraint strap or band 16 is shown secured to the first and second sides of the plate. In one prior art embodiment, the restraint strap may consist of a first portion 18 having one end secured to the first side of the plate and a second portion 20 having a first end secured to the second side of the plate. The opposite ends of the first or second portions may be secured by a way of a knot 22 or other fastening means generally known in the art. FIG. 1 also shows a prior art dressing or trach draining sponge 24.

Figure 2:
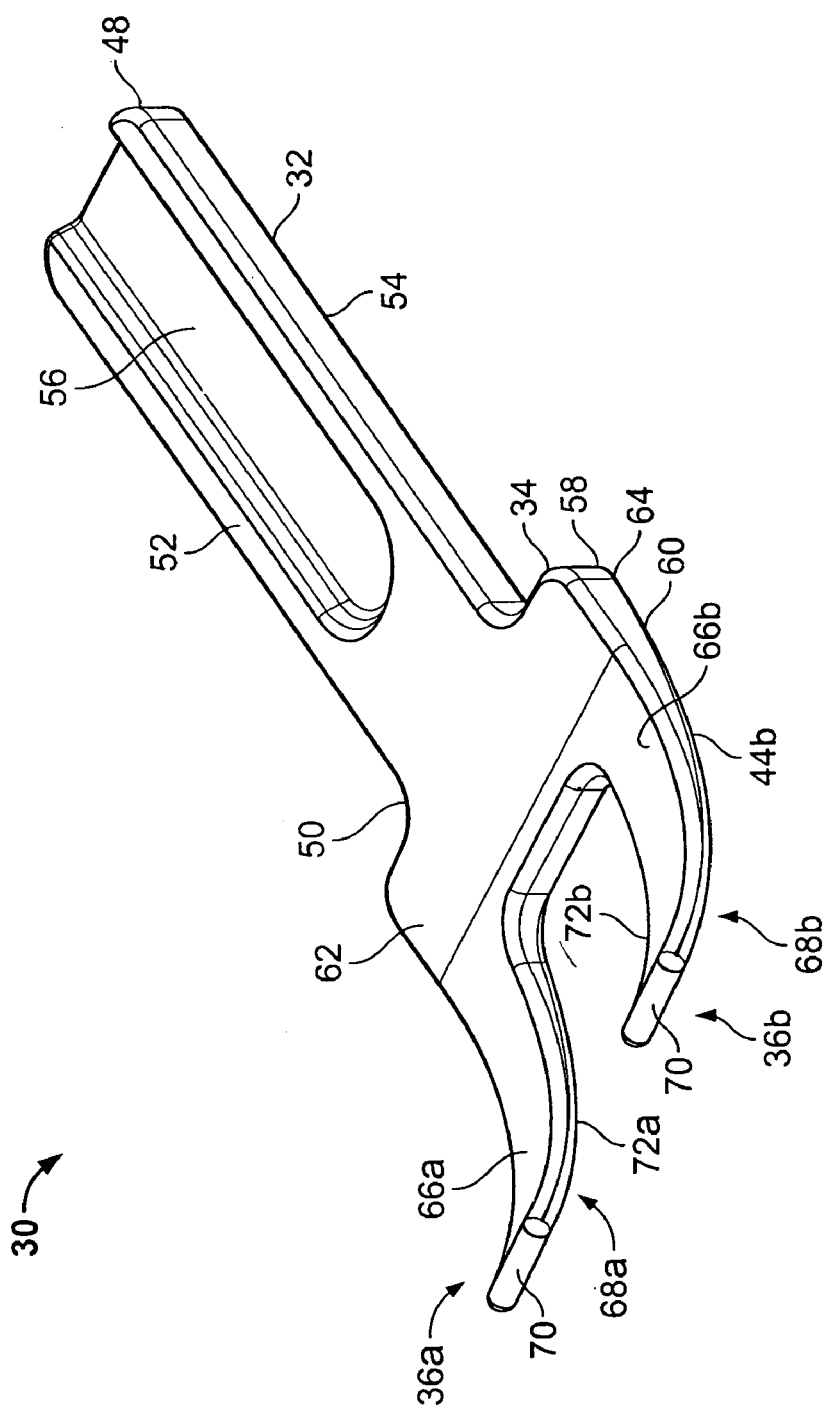
FIG. 2 is a left front perspective view of the device.
Figure 4:
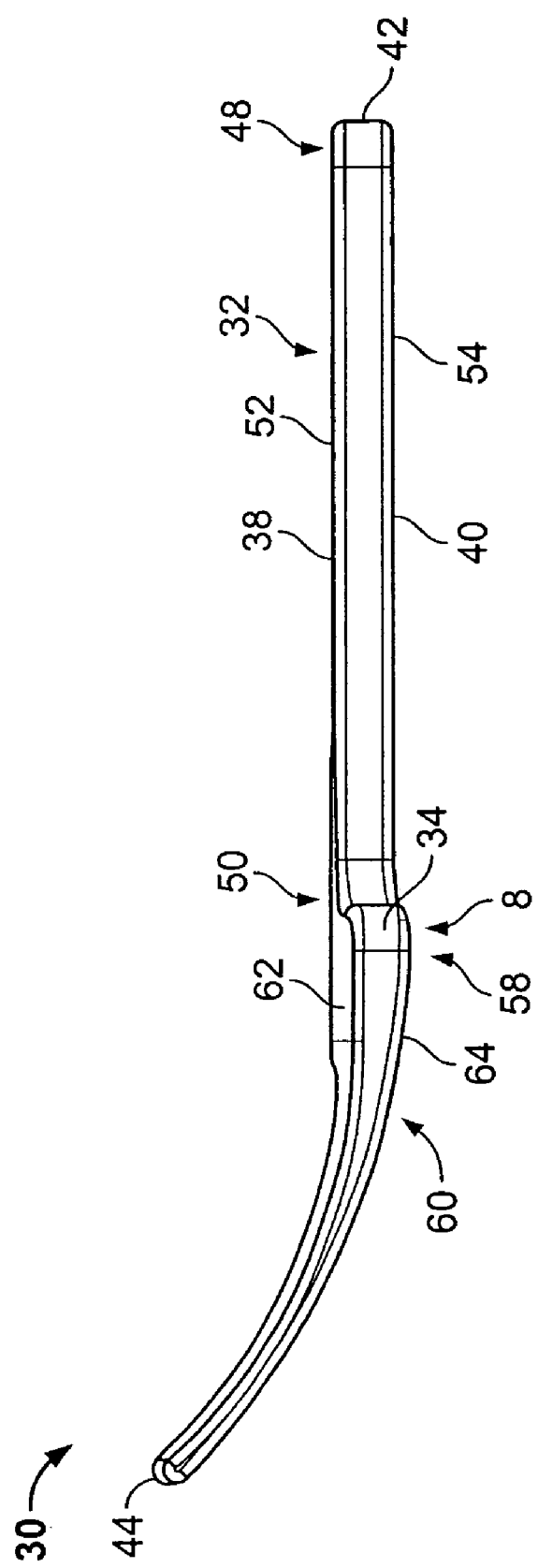
FIG. 4 left side plan view of the device.
Figure 5:
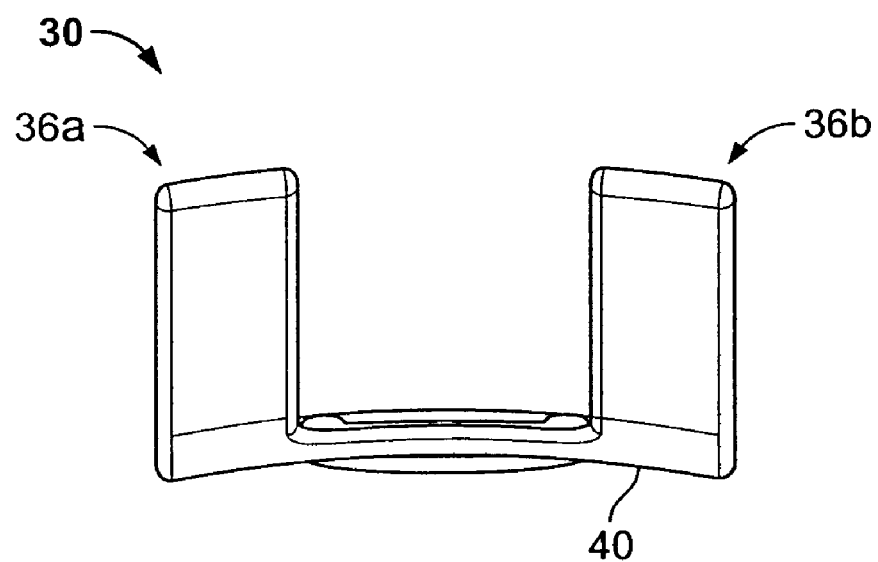
FIG. 5 is a front plan view of a portion of the shoulder and the prongs.
Figure 6:
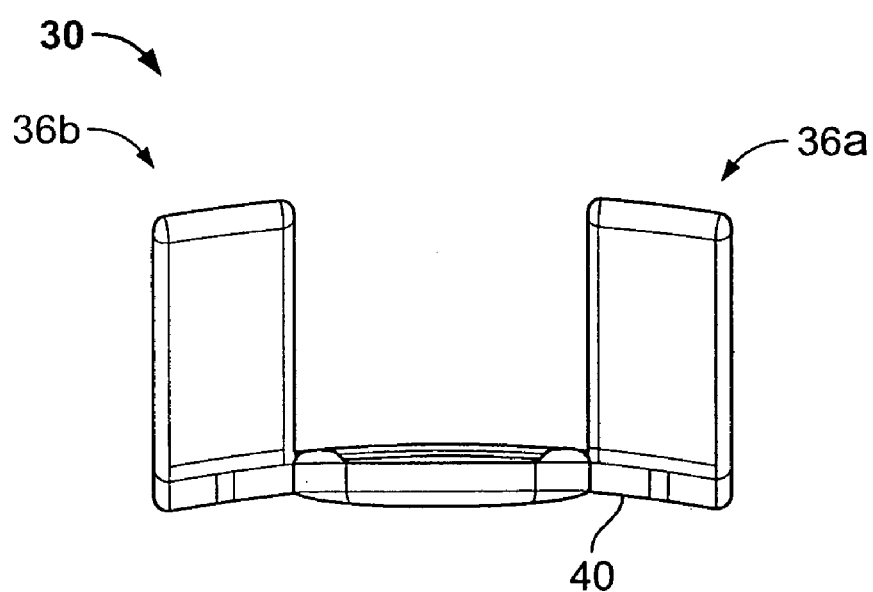
FIG. 6 is an end view of the device.

FIG. 2 is a left front perspective view of one embodiment of the device 30 of the present invention. The device or body 30 includes the handle 32, the shoulder or base 34 and the two prongs 36a, 36b. In one embodiment, the device 30 is made of a molded plastic, but other, inert materials can be used. As can be seen in FIG. 4, the device 30 has an upper surface 38 and a lower surface 40. The body also has a proximal end 42 and a distal end 44.

With reference to FIGS. 2–6, the handle 32 has a proximal end 48, a distal end 50, a top side 52 and a bottom side 54. In one preferred embodiment, as seen in FIG. 2, the top side 52 includes a gripping mechanism or thumb recess 56, however, the gripping mechanism 56 also could be located on the bottom side 54, located within the shoulder 34 or in a variety of other places. In addition, other gripping mechanisms including rubber grips, finger grooves or any of a variety of others may be used in other embodiments.

At the distal end 50 of the handle 32, the shoulder 34 begins. The shoulder 34 can be seen most clearly in FIG. 2. The shoulder 34 has a proximal end 58, distal end 60, a top side 62 and a bottom side 64. Although not shown, the shoulder 34 may include a gripping mechanism such as a thumb recess, rubber grips, finger grooves or any of a variety of other mechanisms on its top side 62 or bottom side 60 in other embodiments. The shoulder 34 may include a gripping mechanism, if the handle 32 is omitted and the shoulder 34 serves as the handle. In another embodiment, the handle is tapered, with the proximal end wider than the distal end.

The distal end 60 of the shoulder has two prongs 36a, 36b extending in a distal direction. While in this preferred embodiment, the prongs are smooth because of the design of the trach drainage sponge 24 associated with the device 30, in other embodiments, the prongs may be different shapes or textures. The prongs have a top side 66a, 66b and a bottom side 68a, 68b. The prong tips are shown to each have a flat edge 70. However, the prongs may have curved edges (not shown). The prongs also curve in an upward direction towards the distal end relative to the shoulder 34 and the body 30. This upward curve can be seen clearly in FIGS. 2 and 4.

Figure 3:
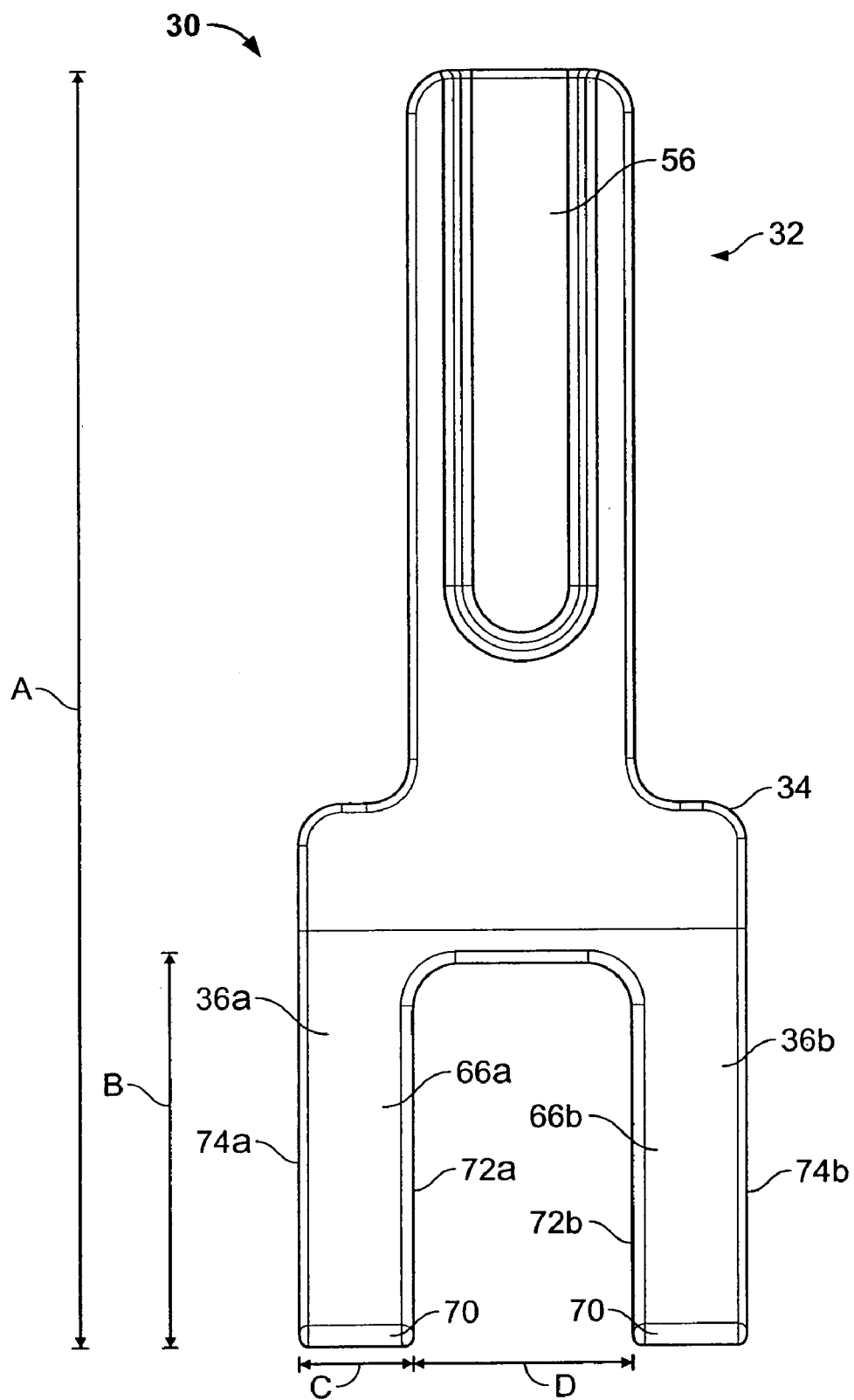
FIG. 3 is a top plan view of the device.

The prongs each have an inside edge 72a, 72b and an outside edge 74a, 74b. The prongs form a primarily "U"-shape as can be seen in FIG. 3. The inside edges 72a, 72b of the prongs are separated by a distance that is greater than the diameter of the tracheostomy tube 10 so that the prongs easily will fit over the tube.

It will be appreciated from FIG. 3 that the prongs 36a, 36b can be considered to continue or extend into the shoulder 34.

In the preferred embodiment, the entire lower surface 40 of the body 30 has a concave shape. This concave shape can be seen in FIGS. 5 and 6. In other embodiments (not shown), however, the concave shape of the lower surface 40 can be limited to the bottom side 64 of the shoulder 34 and prongs 36a, 36b or just the bottom side 68a, 68b of the prongs 36a, 36b. The profile of the concave shape is designed to conform to the profile or shape of a patient's neck.

Figure 7:
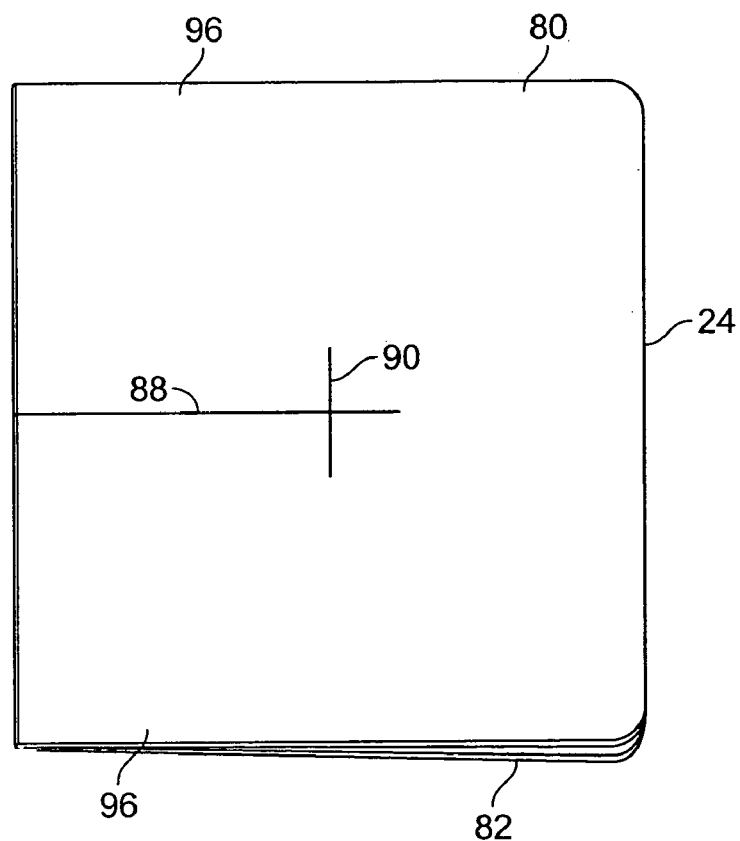
FIG. 7 is a perspective view of the trach drainage sponge in the closed or folded position.
Figure 8:
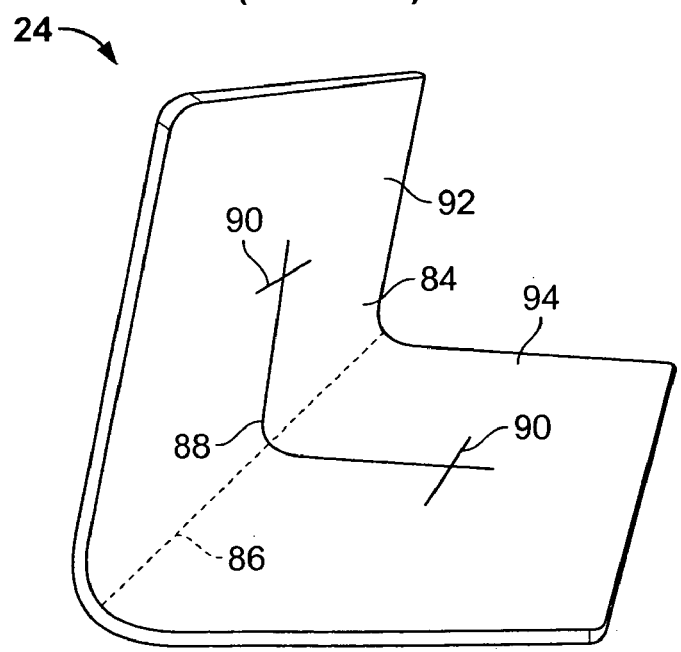
FIG. 8 is a perspective view of the trach drainage sponge in a partially open position.

A prior art trach drainage sponge 24 is shown in FIGS. 7 and 8. In one prior art embodiment, the sponge 24 is made of two-ply absorbent and strong cotton which is folded over itself, creating four layers of absorbency. FIG. 7 shows the sponge in a close position, similar to the manner in which the sponge is packaged and shipped. The sponge includes a top side 80 and a bottom side 82. FIG. 8 shows the sponge in a partially open position and shows the inside surface 84, a seam or pocket 86, a longitudinally extending slit 88 and two transverse slits 90. The seam defines an upper sheath 92 and lower sheath 94. The upper sheath is folded along the seam upon the lower sheath, wherein the transverse slits are aligned with one another when in the closed position shown in FIG. 7. FIG. 7 shows that with the sponge in the closed position, the slits 88, 90 form slats 96.

FIG. 3 shows the overall length A of the device, the length B of the prongs, the width C of the prongs, and the width D between the prongs. In one embodiment, the overall length A is 5 inches, the prong length B is 1¼ of an inch, the prong width C is ½ inch and the width D between the prongs is 1 inch. However, it is believed that other dimensions would work such as a overall length A of 4–6 inches, a prong length B of 1½–2½ inches, a prong width C of ¼ to ¾ of an inch and a width D between the prongs of ¾ to 1½ inches. In general, it is desirable that the width B only be slightly greater than the diameter of the tube. In addition, it is desirable that the width C of the prongs be wide enough so as to assist in advancing the sponge and doing so without piercing the sponge material. However, it is also desirable that the width C of the prongs not be so great as to interfere with the ability of sliding the device under the plate and strap.

Figure 9:
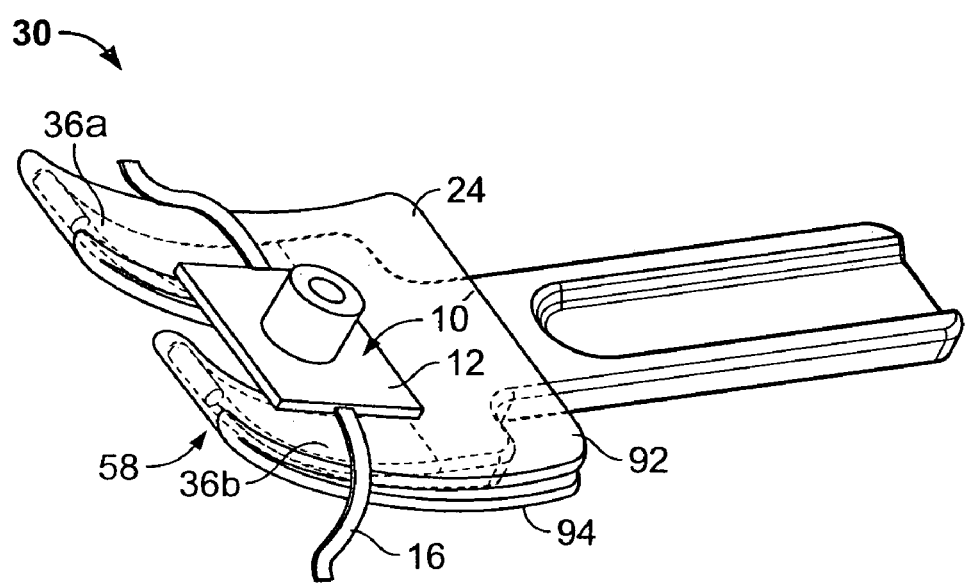
FIG. 9 is a perspective view of the device of the present invention shown in a position wherein the sponge has been inserted about a tracheostomy tube.

The use or operation of device will now be explained. FIG. 9 is a perspective view of a trach drainage sponge having been inserted into position about a tracheostomy tube 10, using a device of the present invention. Initially, the upper sheath and lower sheath are separated from one another from the closed position, either by the user or by the initial insertion of the prongs. The prongs may be inserted between the upper sheath and lower sheath, until the flat edges of the prongs come into contact with the seam or pocket 58. As mentioned before, the prongs may have curved edges. It is important that the design of the prong edges do not pierce the sponge. The slits extend within an area between the prong inside edges. With the device in position between the sheaths, the user may find it advantageous to pinch the sponge about the device so as to maintain control of the device and sponge as the user inserts the sponge into position. The user may prefer to pinch the sponge at the shoulder or perhaps at the distal end of the handle. As the user urges the device about the tracheostomy tube, the flat (or curved) edges of the prongs reside within the seam or pocket and urge the sponge about the tracheostomy tube. Initially, the slit 88 will naturally separate as the slit 88 is engaged by the tracheostomy tube. Further forward movement of the device will allow the sponge to advance along the tracheostomy tube. The user will stop advancing the device and sponge at the time the transverse slits 90 are generally on opposing sides of the tracheostomy tube. During application of the sponge and device to the patient and tracheostomy tube, the user will initially begin with the device held with the distal end of the prongs in a generally parallel relationship to the shoulder of the tracheostomy tube. In contrast, due to the curvature of the prongs, the handle will be extending at roughly a 45 degree angle with respect to the plane of the plate of the tracheostomy tube. As the user advances the device and sponge underneath the plate of the tracheostomy tube and band, the user will bring the handle downward in a manner so as to maintain a substantially parallel relationship with the tangent formed by the portion of the prongs directly underneath the shoulder of the tracheostomy tube. Once the sponge is in position about the tracheostomy tube, the user may hold the sponge in place while withdrawing the device from the sponge and tracheostomy tube.

It will be readily apparent that the device may be modified to be adapted for various styles and sizes of the trach drain sponge. For example, the trach drainage sponge might not include an upper and lower sheath. The device, as disclosed, may still function with the sponge or may require some modification from the preferred embodiment described and shown herein, without departing from the spirit of the invention.

The invention claimed is:

1. A device for the application of a trach drainage sponge between a trach apparatus and a patient's neck, the trach apparatus including a trach having a diameter and the sponge including an upper sheath and a lower sheath, the applicator device comprising:
   a body having an upper surface, a lower surface, a proximal end and a distal end;
   a handle located within the body, the handle having a proximal end and distal end, the proximal end being the proximal end of the body;
   a shoulder located at the distal end of the handle; and
   two prongs extending distally from the shoulder and curving in an upward direction relative to the body, the prongs having a gap between them, each prong having a length and a width, whereby each prong is adapted to engage the sponge and is shaped to fit between the trach apparatus and the patient's neck and with the trach between the prongs.

2. The device of claim 1 wherein each prong has an inner edge and an outer edge and the gap is between the inner edges of the prongs, wherein the prongs are parallel and form a "U"-shape, and the gap is greater than the trach diameter.

3. The device of claim 1, wherein each prong includes a flat edge adapted to engage the sponge.

4. The device of claim 1, wherein the lower surface has a concave shape.

5. The device of claim 1, wherein the length of the prongs is in the range of one and one-half inch to two and one-half inch, the prong width is in the range of one-quarter inch to three-quarter inch, and the length of the gap between the prongs is in the range of the three-quarter to one and one-half inch.

6. The device of claim 1, wherein the length of the prongs is one and three-quarter inch, the prong width is one-half inch, and the length of the gap between the prongs is one inch.

7. A device for the application of a trach drainage sponge between a trach apparatus and a patient's neck, the trach apparatus including a trach having a diameter and the sponge including an upper sheath and a lower sheath, the applicator device comprising:
   a body having an upper surface, a lower surface, a first side and second side, a proximal end and a distal end, the lower surface having a concave shape extending from the concave first side to the second side;
   a handle located within the body, the handle having a proximal end and distal end, the proximal end being the proximal end of the body;
   a shoulder located at the distal end of the handle; and
   two prongs extending distally from the shoulder and curving in an upward direction relative to the body, whereby each prong is adapted to engage the sponge and is shaped to fit between the trach apparatus and the patient's neck and with the trach between the prongs.

8. The device of claim 7 wherein each prong has an inner edge and an outer edge and the inner edges are separated by a width distance greater than the trach diameter.

9. The device of claim 8 wherein the prongs are parallel and form a "U"-shape.

10. The device of claim 9 wherein the handle includes a gripping mechanism.

11. A device for the application of a trach drainage sponge between a trach apparatus and a patient's neck, the trach apparatus including a trach with a diameter and the sponge including an upper sheath and a lower sheath, the applicator device comprising:
    a base having an upper surface, a lower surface, a proximal end and a distal end, the lower surface having a concave shape; and
    two prongs extending from the distal end in a distal direction and curving in an upward direction relative to the base whereby each prong is adapted to engage the sponge and is shaped to fit between the trach apparatus and the patient's neck, with the trach between the prongs.

12. The device of claim 11 wherein each prong has an inner edge and an outer edge and the inner edges are separated by a width distance greater than the trach diameter.

13. The device of claim 12 wherein the prongs are parallel and form a "U"-shape.

14. The device of claim 11 wherein the base has a gripping mechanism.

15. A device for the application of a trach drainage sponge where the sponge is placed between a trach apparatus and a patient's neck, the trach apparatus including a trach with a diameter and the sponge including an upper sheath and a lower sheath, the device comprising:
    a body portion with an upper surface and a lower surface, where the lower surface is curved opening in a downward facing direction; and
    two prongs attached to the body portion, each prong having a top side and a bottom side, the prongs extending away from the body and curved where the top side of the prongs open in an upward facing direction, opposite to the direction of the curve of the lower surface of the body.

16. The device of claim 15 wherein each prong has an inner edge and an outer edge and the inner edges are separated by a width distance greater than the trach diameter.

17. The device of claim 16 wherein the prongs are parallel and form a "U"-shape.

18. The device of claim 15 wherein the base has a gripping mechanism.

19. A non-invasive method for applying a trach drainage sponge between a trach apparatus and a patient's neck, the trach apparatus including a trach having a diameter, the method comprising the steps of:
    gripping a device having two prongs, each prong extending in the distal direction and an upward direction relative to the handle and spaced apart a distance greater than the trach diameter;
    inserting the prongs into the sponge;
    inserting the prongs and the sponge between the trach apparatus and the patient's neck whereby the sponge rests between the trach and the patient's neck; and
    removing the prongs from the sponge.

20. The method of claim 19 wherein the prongs extend in a curved upward direction and wherein the prongs and the sponge are inserted between the trach apparatus and the patient's neck in an arcing direction.

21. The method of claim 19 wherein the trach apparatus is held in position against the patient's neck by a restraint apparatus and simultaneously with insertion of the prongs and the sponge, the restraint apparatus is slightly shifted from its normal position to facilitate the insertion of the prongs and the sponge between the trach apparatus and the patient's neck.

22. The method of claim 19 wherein the sponge includes an upper sheath and a lower sheath, wherein the step of gripping includes pinching the upper sheath and the lower sheath against the device.

23. The method of claim 22 wherein the upper sheath of the sponge is placed upon and balances on each prong prior to the pinching step.

24. A device for the application of a trach drainage sponge between a trach apparatus and a patient's neck, the trach apparatus including a trach having a diameter and the sponge including an upper sheath and a lower sheath, the applicator device comprising:
    a handle having a proximal end and distal end;
    a shoulder located at the distal end of the handle, the shoulder including a top side and a bottom side; and
    two prongs extending distally from the shoulder and curving in an upward direction relative to the handle, the prongs having a gap between them, each prong having a length and a width, the length of the prongs is one and three-quarter inch, the prong width is one-half inch, and the gap between the prongs is one inch, whereby each prong is adapted to engage the sponge and is shaped to fit between the trach apparatus and the patient's neck and with the trach between the prongs.

* * * * *